United States Patent [19]

Baker

[11] Patent Number: 4,890,688
[45] Date of Patent: Jan. 2, 1990

[54] ANECHOIC EAR PIECE

[76] Inventor: David Baker, 15 W. Notredame, Glens Falls, N.Y. 12801

[21] Appl. No.: 338,240

[22] Filed: Apr. 14, 1989

[51] Int. Cl.⁴ .......................................... H05R 25/00
[52] U.S. Cl. ...................................... 181/136; 181/129
[58] Field of Search ............... 181/129, 130, 136, 133

[56] References Cited

U.S. PATENT DOCUMENTS

| | | | |
|---|---|---|---|
| 656,182 | 8/1900 | Ehrhardt | 181/136 |
| 1,453,969 | 5/1923 | Brown | 181/130 X |
| 1,708,257 | 4/1929 | Campbell | 181/136 |
| 2,469,254 | 5/1949 | Bankson | 181/136 |
| 2,537,201 | 1/1951 | Amfitheatrof | 181/136 |
| 2,977,426 | 3/1961 | Noyes et al. | 181/129 |
| 3,139,150 | 6/1964 | Weil | 181/136 |
| 3,618,698 | 11/1971 | McCabe | 181/136 |
| 3,658,150 | 4/1972 | Turner | 181/136 |
| 3,938,616 | 2/1976 | Brownfield | 181/136 |
| 4,574,912 | 3/1986 | Fuss et al. | 181/136 |
| 4,768,613 | 9/1988 | Brown | 181/136 |
| 4,771,859 | 9/1988 | Breland | 181/136 |

*Primary Examiner*—B. R. Fuller
*Attorney, Agent, or Firm*—Schmeiser, Morelle & Watts

[57] ABSTRACT

An anechoic ear piece for placement about a human ear. The internal surface of the ear piece is lined with acoustic foam to prevent sound wave from reflecting off of the inner surface of the ear piece into the human ear. Furthermore, the ear piece is cone shaped with the apex of the cone adapted to lie opposite the listener's ear whereby sound waves entering the ear piece but not entering the ear itself directly, will impact on the inner surface of the ear piece wherein those waves not absorbed will be reflected toward other inner surfaces of the ear piece where continued absorption will take place.

6 Claims, 2 Drawing Sheets

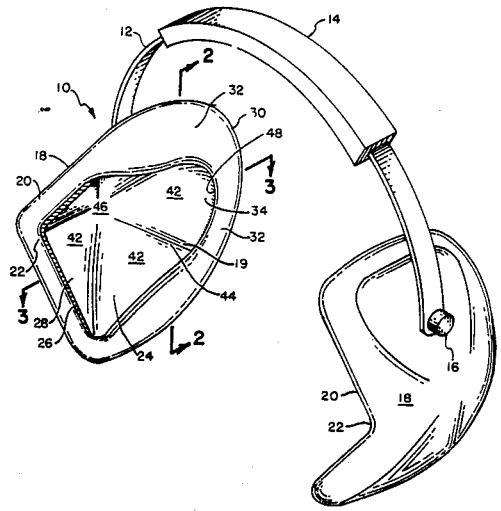

4,890,688

ANECHOIC EAR PIECE

FIELD OF THE INVENTION

Generally this invention relates to ear pieces which are utilized to effect an individuals hearing. More specifically, this invention is an ear piece which enhances ones ability to listen to stereophonic music by suppressing echoes and sound wave reflection.

BACKGROUND OF THE INVENTION

Ear pieces which are secured in close proximity to a persons ear in order to effect sound input are well known. Numerous patents have issued directed toward myriad variations upon the basic theme of sound amplification through the use of a mechanical ear cup.

Patents such as those issued to Amfitheatrof, Pat. No. 2,537,201; Brown, Pat. No. 4,768,613; Fuss et al, Pat. No. 4,574,912, as well as most of the prior art patents have has their purpose the amplification of sound. In order to amplify sound it is by its very terms necessary to direct additional sound waves into the ear which would not normally enter therein. This is accomplished by blocking sound waves which would normally bypass the ear and reflecting them into the ear. Thus, these ear cups serve as sound wave gatherers and direct these additional sound waves into the human ear in order to amplify the sound. These ear cups of necessity utilize reflective surfaces of whatever configuration they believe which will most readily gather and redirect the sound into the human ear and thus these ear cups function in a manner very similar to an echo chamber.

These types of devices create an environment which is contrary to that which is desired when listening to stereophonic music. As is well known, in any professional theater or music hall, the primary auditory goal is to enable the listener to clearly hear the distinct sounds as they come from the performers or instruments with little or no reflection from the walls, ceilings or other portions of the buildings. When this is successfully accomplished, the listener is able to distinguish, as for an example with an orchestra, the various instruments and where they are located while the music connoisseur is able to further distinguish tones of particular instruments as well as whether a particular instrument is in unison with the rest of the orchestra.

Where an environment results in the reflection of sound waves several phenomena exist all of Which distort the actual sounds. First, sound waves which reflect off the wall will encounter either sound waves emanating from the source or else other reflected sound waves. This results in either a standing wave which cancels the sound wave emanating from the speaker or else the combination of the sound waves which distorts the speaker sound wave. Secondly, sound waves reflected off of a surface reach the listener's ear out of phase with those sound waves that travel directly from the speaker to the listeners ear. These out of phase sound waves prevent the listener from distinguishing between proper and improper timing as well as preventing him from determining the origin or location of a particular voice or musical instrument sound.

Nevertheless, the prior art devices all gather sound by reflecting or redirecting sound waves and therefore they all create, to varying degrees, sound wave distortion and out of phase sound impressions. By reflecting or redirecting sound waves to the listener these devices also create an effective increase in volume to the listener which has an interesting effect on the perception of the listener. More particularly, any increase in volume will generally be perceived by the relatively inexperienced listener to result in an increase in clarity. In fact however, there is no increase in clarity. This may be shown by questioning the listener regarding the characteristics of the composition, such as instrument placement, tone of particular instruments and unity, of the music being played. The listener will be unable to answer these questions accurately because there is in fact no improvement in clarity with simple volume increases. Nevertheless, because the increase in volume draws the listeners attention away from the more subtle aspects of the musical composition, the existing errors or inconsistencies tend to be blocked out resulting in the misconception that clarity has been improved.

The patent to M. Weil, U.S. Pat. No. 3,139,150 recognizes the need to block the reception, by the ear, of sound waves reflecting from the walls, ceilings or other reflective surfaces in the listener's environment. However, the sound interceptors of Weil also serve as points of reflection since sound waves directed toward the ear will be reflected off of the honeycomb sound entry apertures and the outside wall. This configuration will result in a reverberation that Weil attempts to prevent by using release apertures. Nevertheless, Weil, as all the other patents, indicates that there is a volume increase which volume is of necessity increased due to the sound gathering effect of the device which inherently means out of phase sound waves and multiple sound wave interference.

When testing speakers and other sound or wave transmitting devices it is common to use an anechoic chamber. These chambers are generally comprised of a plurality of cone shaped, sound absorptive pylons which extend, from virtually all points of the walls, ceiling and floor of the chamber outwardly into the room. The purpose of these pylons is to absorb all of the sound waves which impact thereon so that a receiver within the chamber can measure the true and accurate characteristics of the sound waves for analysis of the quality of the transmitter. In such a chamber there is obviously no sound amplification since the only sound waves impacting on the receiver are those which emanate directly from the transmission source. Assuming good quality speakers, a person listening to an orchestra recording in an anechoic chamber would have virtually the same auditory experience as if listening to the orchestra live when seated central to the orchestra and in a quality music hall where sound reflections are virtually eliminated. In such an environment virtually each and every group of instruments, as well as instruments in each group, can be clearly discerned as can their location relative to the rest of the orchestra.

Unfortunately, such optimum conditions were not previously available for the average or even non average music lover.

SUMMARY OF THE INVENTION

The subject invention functions by creating an anechoic chamber about the ear with an opening in said chamber to receive only direct sound waves emanating from the stereo speakers. This effect is accomplished by two primary characteristics of the subject invention. First, the inner surface of the ear piece is lined with an acoustic foam for absorbing sound waves and thereby limiting reflections. Secondly, the ear pieces are cone shaped with the apex of the cone being opposite the listener's ear. This cone shape results in the cross cancellation of sound waves which are not absorbed by the acoustic foam and impact on the inner surface of the ear piece thus preventing the sound waves from entering the listener's ear.

Other features aid in the accomplishment of the desired purpose such as using a flange which encapsulates the top rear and bottom of the ear such that the ear is contacting the inner surface and there is virtually no space beyond the ear, in the plane of the ear, which could serve as a sound wave reflector. Also, the cone shape will direct sound waves not initially absorbed by the acoustic away from the listener's ear and toward other foam covered surfaces.

Other benefits of this invention will be recognized by those familiar with this field after reading the subject disclosure and through practice with the invention.

DETAILED DESCRIPTION OF THE INVENTION

Figure 1:
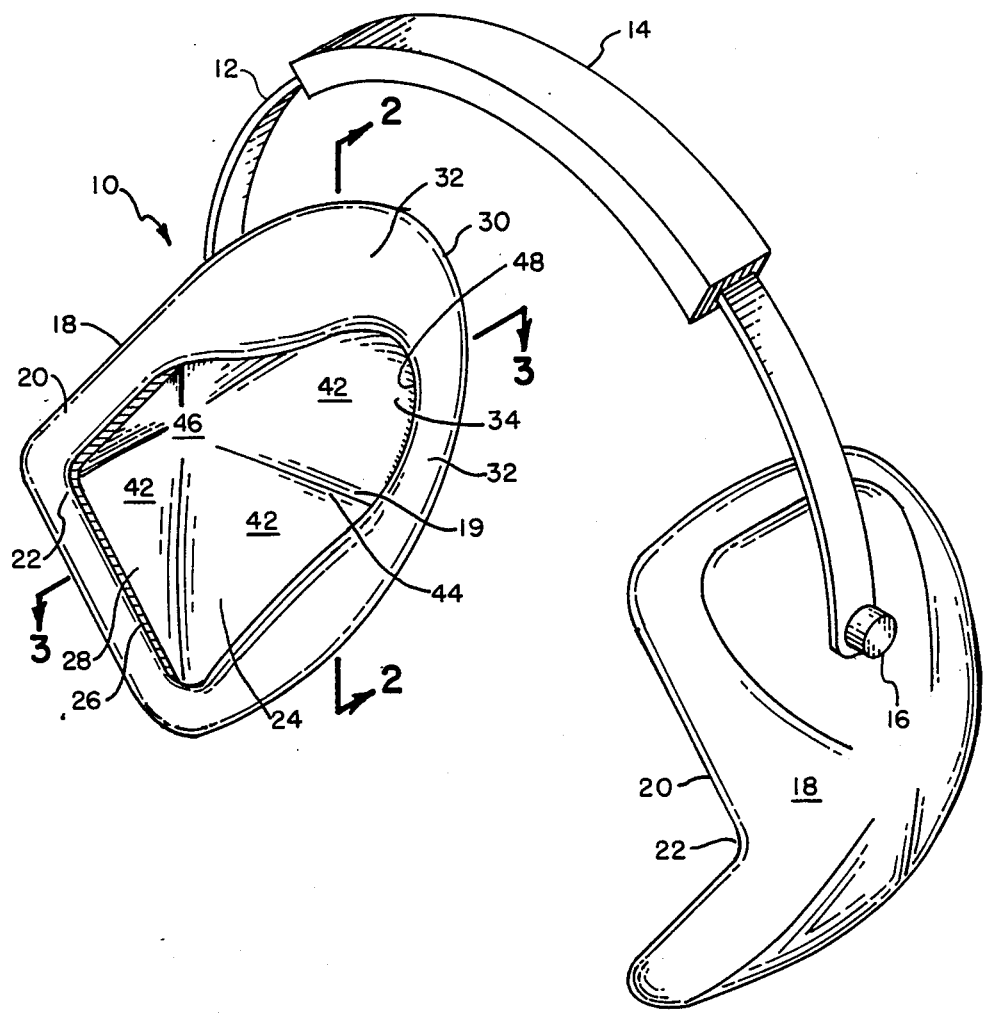
FIG. 1 is a front perspective view of the invention.

FIG. 1 discloses the anechoic ear piece generally designated as 10. As is the case with most headphones two anechoic ear pieces, one for the left and one for the right, are joined by bands 12 which are slidably secured within a retainer 14. The ear pieces 10 are rotatably secured to the bands 12 by securing pins 16. This enables the wearer to rotate the ear pieces 10 in the direction of the sound wave source. Also, if desired one could fashion the ear piece with a variable sized front opening or cutaway 22 so the ear piece entry could be adapted to the particular speaker arrangement being used.

Each ear piece has a body portion 18 which is cone shaped. For the purposes of this application it will be appreciated that the inner circumference of the cone need not have a uniform curvature and in fact it is often preferable to have flat panel sections which are relatively triangular in shape joined to adjacent panels along the side edges 19 forming a small curved area. The front portion 20 of the body has a "V" shaped cutaway 22 which opens into the cavity 24 formed by said body portion. The mouth perimeter 26 which runs along the "V" shaped cut away 22 is flush with the inner surface 28 of the body 18 so that there is no wall for reflecting sound. The remaining perimeter of the body portion 18 is a predetermined segment 30 which lies in a singular plane and extends along the top, back and bottom portions of the ear.

A flange 32 extends inwardly from said predetermined perimeter segment and lies beneath the outwardly extending portions of the ear such that there is virtually no space behind the ear at point 34. With this configuration, sounds are not reflected off the back portion of the ear piece.

Figure 2:
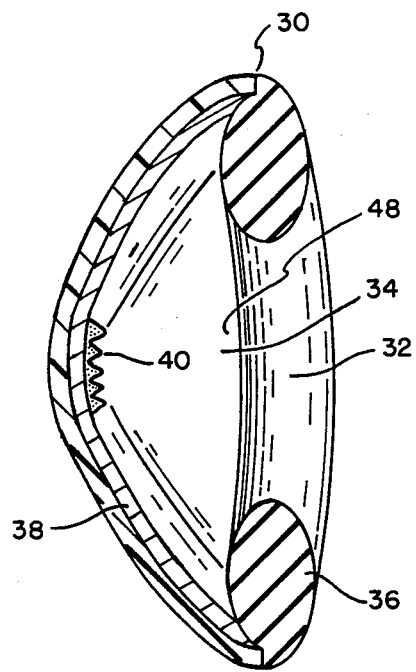
FIG. 2 a cross sectional view taken along lines 2—2 of FIG. 1.
Figure 3:
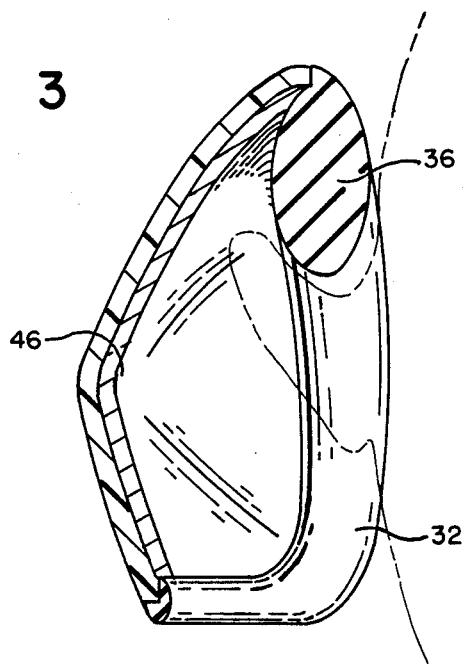
FIG. 3 is a cross sectional view taken along lines 3—3 of FIG. 1.

As shown in FIGS. 2 and 3 the inner portion of the flange 32 is made of padding 36 and covered by vinyl. The inner surface 28 of the body 18 is lined with an acoustic foam 38 which may be made of a cellulose foam or any other suitable material. I have found that for most applications acoustic foam one eighth of an inch thick is sufficient. However, one may increase the thickness and thereby increase the degree of sound wave absorption. Also, in an alternate embodiment one may incorporate small foam covered pylons 40 (similar in function to those used in an anechoic chamber) within the ear piece in order to further suppress sound wave reflection.

In my preferred embodiment the inner surface 28 is comprised of a unitary body which is formed of a plurality of adjacent triangular planar panels 42 with a slight area of curvature 44 between the planar panels. The panels join each other at their top most segments at a pinnacle 46 which pinnacle is the furthest most portion of the inner surface from the listener's ear. The planar panels extending downwardly from the pinnacle 46 terminate at the mouth perimeter 26 and predetermined perimeter segment 30. In this configuration there is virtually no surface parallel to the plane of the user's ear.

In operation the user slides the ear piece over the ears from the back. The flange 32 slips beneath the extended portions of the ear with the ear piece being fit into place when the ear rests against the rear most section 48 of the ear piece.

The bands 12 are slid within their retainer until the proper adjustment is obtained at which point the ear pieces 10 are rotated about the securing pin 16 until the "V" shaped cutaway 22 is directed substantially toward the audio transmitter. As music is played, the direct sound waves will enter through the "V" shaped cutaway 22 and be received by the listener's ear. Those sound waves which enter the cavity 24 that are not directed toward the listener's ear will impact upon the inner surface 28 where most of the sound waves will be absorbed by the acoustic foam 38. Those sound waves which are not absorbed will be reflected either toward the pinnacle 46 or toward other planar panels 42 where they will interact with other reflected sound waves with the resultant cancellation of virtually all the sound waves as they continue to be absorbed by the acoustic foam. It is most important to note that the sound waves which are reflected will not be directed toward the users ear in any significant quantity since there are virtually no surfaces parallel to the listener's ear which parallel surfaces are the most conducive for reflecting sound waves into the ear.

While the above describes the preferred embodiment of the subject invention it should be appreciated that many variations can be made without departing from the scope of the teachings of the invention incorporated herein. Therefore, it is not intended that the scope of this invention be limited in any way by the Detailed Description but only by the claims appended hereto.

What is claimed is:

1. An anechoic ear piece comprising:
   an ear piece body adapted to be placed over a human ear, said body extending upwardly from a perimeter thereof such that a pinnacle of the body is held in a spaced apart relation opposite said ear, and forming a cavity about said ear, a portion of the body being cut away forming an exterior opening into said cavity;
   a padding provided about a predetermined portion of the perimeter adapted to contact a user; and
   a lining of acoustic foam on an inner surface of said ear piece body for absorbing sound waves impacting said inner surface, wherein said inner surface extends downwardly from the pinnacle toward the perimeter forming a cone shaped inner surface.

2. The invention of claim 1 wherein the cutaway opening is "V" shaped.

3. The invention of claim 1 further comprising:
a flange extending inwardly from a predetermined portion of the perimeter whereby said flange engages the ear when the ear piece is in place.

4. An anechoic ear piece comprising:
an ear piece body adapted to be placed over a human ear, said body extending upwardly from a perimeter thereof such that central portion of the body forms a Pinnacle and is held in a spaced apart relation from said ear, and forming a cavity about said ear, a portion of the body being cut away thereby forming an exterior opening into said cavity;
a plurality of substantially planar panel sections forming a unitary cone shaped inner body surface.

5. The invention of claim 4 wherein the opening into said cavity is "V" shaped.

6. The invention of claim 4 further comprising a flange extending inwardly from a predetermined segment of the perimeter, said flange engaging the ear when the ear piece is placed on a user.

* * * * *